United States Patent [19]

Yim et al.

[11] Patent Number: 5,098,659
[45] Date of Patent: Mar. 24, 1992

[54] APPARATUS FOR CONTINUOUSLY MONITORING A PLURALITY OF CHEMICAL ANALYTES THROUGH A SINGLE OPTICAL FIBER AND METHOD OF MAKING

[75] Inventors: Jeffrey B. Yim, Woodinville; Gamal-Eddin Khalil, Bellevue, both of Wash.; Roger J. Pihl, San Francisco, Calif.; Bradley D. Huss, Snohomish, Wash.; Gerald G. Vurek, Mountain View, Calif.

[73] Assignee: Abbott Laboratories, Abbott Park, Ill.

[21] Appl. No.: 587,234

[22] Filed: Sep. 24, 1990

[51] Int. Cl.$^5$ .................. G01N 21/00; A61B 5/00
[52] U.S. Cl. .................. 422/82.07; 422/82.06; 128/634; 358/12; 427/2
[58] Field of Search .............. 422/82.06, 82.07; 128/634, 636; 350/96.29; 356/39; 427/2

[56] References Cited

U.S. PATENT DOCUMENTS

| | | | |
|---|---|---|---|
| 4,272,484 | 6/1981 | Lübbers | 422/82.07 |
| 4,785,814 | 11/1988 | Kane | 128/634 |
| 4,895,156 | 1/1990 | Schulze | 128/634 |
| 4,925,268 | 5/1990 | Iyer et al. | 350/96.29 |
| 4,929,049 | 5/1990 | Le Goullon et al. | 350/96.29 |
| 4,929,561 | 5/1990 | Hirschfeld | 422/82.06 |
| 5,006,314 | 4/1991 | Gourley et al. | 350/96.29 |
| 5,019,350 | 5/1991 | Rhum et al. | 422/82.07 |

Primary Examiner—Robert J. Warden
Assistant Examiner—Theresa A. Trembley
Attorney, Agent, or Firm—Christensen, O'Connor, Johnson & Kindness

[57] ABSTRACT

A $CO_2/O_2$ or $pH/O_2$ gas sensor comprising a single optical fiber and a method for making the same. The optical fiber carries light signals at different wavelengths for monitoring either $CO_2$ concentration or pH level, in combination with $O_2$ concentration. Attached to the distal end of the fiber-optic probe is a cylindrical pellet that has one surface covered by a light reflective material (gold foil) and the other surface attached adjacent to the distal end of the optical fiber. Depending on whether the sensor is to monitor either $CO_2$ or pH, the pellet comprises either a $CO_2$ analyte indicator molecule or a pH analyte indicator molecule covalently bonded to a polymer matrix material. Also adjacent to the distal end of the optical fiber is disposed a second polymer matrix material which is codissolved with an $O_2$ analyte reactive indicator molecule. The second polymer matrix material is either interposed between the cylindrical pellet and the distal end of the optical fiber or surrounds the cylindrical pellet. If pH is being measured, the distal end of the optical fiber is coated with a hydrophilic material that is permeable to water. Conversely, if $CO_2$ is being monitored, the distal end is coated with a hydrophobic material.

44 Claims, 3 Drawing Sheets

000# APPARATUS FOR CONTINUOUSLY MONITORING A PLURALITY OF CHEMICAL ANALYTES THROUGH A SINGLE OPTICAL FIBER AND METHOD OF MAKING

TECHNICAL AREA

This invention relates to fiber-optic sensors suitable for monitoring chemical analyte concentrations and to a method of making such sensors.

BACKGROUND OF THE INVENTION

In recent years, fiber-optic chemical sensors, sometimes called optrodes, have been developed to detect the presence and monitor the concentration of various analytes, including oxygen, carbon dioxide, and pH, in liquids and in gases. Such sensors are based on the recognized phenomenon that the absorbance, and in some cases, the luminescence, phosphorescence, or fluorescence of certain indicator molecules are specifically perturbed in the presence of specific analyte molecules. The perturbation of the luminescence and/or absorbance profile can be detected by monitoring radiation that is absorbed, reflected, or emitted by the indicator molecule in the presence of a specific analyte.

Fiber-optic probes relying upon these characteristics position the analyte-sensitive indicator molecule in a light path at a desired measurement site. Typically, the optical fiber transmits electromagnetic radiation from a light source to the indicator molecule, and the reflectance from or absorption of light by the indicator molecule gives an indication of the gaseous or ionic concentration of the analyte. Alternatively, for monitoring other analytes such as $O_2$, the optical fiber transmits electromagnetic radiation to the indicator molecule, exciting it into phosphorescence, and the level and/or duration of phosphorescence by the indicator molecule serves as an indication of the concentration of that gas in the surrounding fluid. In the prior art probes, the indicator molecules are typically disposed in a sealed chamber at the distal end of the optical fiber, and the chamber walls are permeable to the analytes of interest.

One problem with the known sensing systems of the type described is that the optical fiber and chamber attached to the end of the probe are prone to physical damage. The optical fibers with attached sensing chambers are delicate because they are disposed as an external appendage at the end of the probe, extending distally beyond a catheter through which the probe is positioned inside a patient's circulatory system. Any mishandling of the catheter can easily result in damage to the delicate sensor chamber.

An additional problem with the known sensing systems described above is that the structure of the chambers and probe configuration often encourage the formation of blood clots, or thrombi. Typically the sensors of the prior art contain discrete optical fibers for each blood gas parameter such as $O_2$, pH, and $CO_2$. This multiplicity of fibers adds to the diameter of the complete probe and provides interfiber crevices that encourage thrombi formation. Furthermore, the complexity and difficulty of manufacturing multi-fiber probes is well known, due to the small diameters of the fibers and requirements for their arrangement. Even though a bundled optical fiber probe for sensing a plurality of analytes may have a remarkably small overall cross section, its size can still preclude its use in neonatal or pediatric applications in which the patient's veins or arteries are too small in diameter for insertion of the sensor assembly. Thus, prior art multi-analyte sensors fail to effectively deal with several problems.

SUMMARY OF THE INVENTION

In accordance with the present invention, a probe for monitoring a plurality of chemical parameters includes an optical fiber having a longitudinal axis along which light signals at a plurality of wavelengths are propagated bidirectionally. An optical sensor is attached adjacent to a distal end of the optical fiber and comprises a first analyte indicator. Light signals of a first wavelength are absorbed by the first analyte indicator to an extent dependent upon the concentration of a first analyte present. A second polymer matrix material containing a second analyte indicator is disposed adjacent to the distal end of the optical fiber and adjacent to the optical sensor. Light signals of a second wavelength that are transmitted to the distal end of the optical fiber excite the second analyte indicator to emit light. A decay time for the light emission varies in response to a concentration of the second analyte.

In one embodiment of the probe, the first analyte indicator is sensitive to carbon dioxide concentration. In a second embodiment, the first analyte indicator is sensitive to a pH level. In both embodiments, the second analyte indicator is sensitive to oxygen concentration. The optical sensor can be attached to the distal end of the optical fiber with a thin coat of the polymer matrix material that is provided with the second analyte indicator. In addition, the sensor pellet and the distal end of the optical fiber can be covered with a coating comprising the polymer matrix material and the second analyte indicator.

Preferably, the optical sensor comprises a pellet attached to a transverse surface of the optical fiber at its distal end. In one form of the probe, the pellet covers only a portion of the transverse surface and the polymer matrix material provided with the second analyte indicator encloses the pellet, the transverse surface, and the distal end of the optical fiber.

In another form of the probe, the polymer matrix material, including the second analyte indicator, comprises a layer that is interposed between the optical sensor and the distal end of the optical fiber. Where the first analyte is ionized in water, a hydrophilic coating is applied over the layer of the polymer matrix material that is provided with the second analyte indicator, and over the optical sensor. However, where the first analyte is a gaseous substance, a hydrophobic coating is applied over the layer of the polymer matrix material containing the second analyte indicator, and over the optical sensor. Preferably, the second analyte indicator comprises a porphyrin compound and is substantially unaffected by light signals at the first wavelength.

A method for making a chemical sensor comprises a further aspect of this invention. In accordance with the method, a first polymer matrix is mounted on at least a portion of a distal end of an optical fiber so that light propagating through the optical fiber passes into the first polymer matrix. The first polymer matrix contains a first indicator molecule that absorbs light of a first wavelength in proportion to the concentration of a first analyte. A thin film of light-reflective material is applied adjacent to the first polymer matrix, such that light of the first wavelength propagated distally along the optical fiber and through the first polymer matrix is reflected by the thin film of light-reflective material, back towards a proximal end of the optical fiber. A second polymer matrix is also applied to the distal end of the optical fiber and contains a second molecule that emits light when excited by light of a second wavelength to an extent that is proportional to the concentration of a second analyte disposed around the sensor.

Where the first analyte is carbon dioxide, the method further comprises the step of coating the first polymer matrix and the distal end of the optical fiber with a hydrophobic material. Where the first analyte comprises hydrogen ions, the method further comprises the step of coating the first polymer matrix and the distal end of the optical fiber with a hydrophilic material.

In one form of the method, the second polymer matrix is applied prior to the step of coating the first polymer matrix such that the second polymer matrix is substantially interposed between the distal end of the optical fiber and the first polymer matrix. The first polymer matrix can be applied over only a portion of the transverse area of the distal end of the optical fiber such that light of the second wavelength is incident upon the second polymer matrix through a remainder of the transverse area of the distal end.

BRIEF DESCRIPTION OF THE DRAWINGS

The advantages of this invention will become more readily apparent by reference to the following Detailed Description of the Preferred Embodiments, in conjunction with the accompanying drawings wherein.

DETAILED DESCRIPTION OF THE PREFERRED EMBODIMENTS

Figure 1:
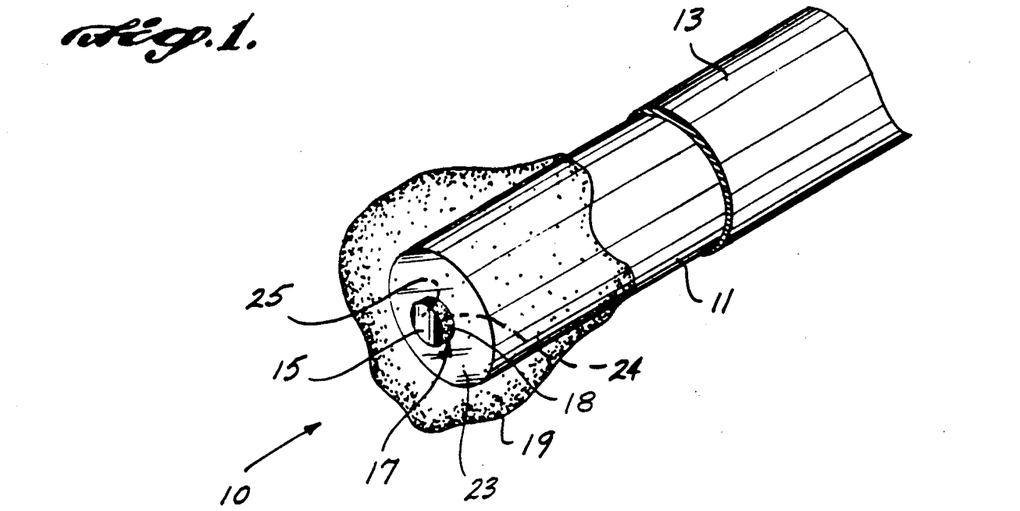
FIG. 1 is an isometric view of a first embodiment of a sensor for determining $CO_2$ and $O_2$ concentration in accord with the present invention.
Figure 2:
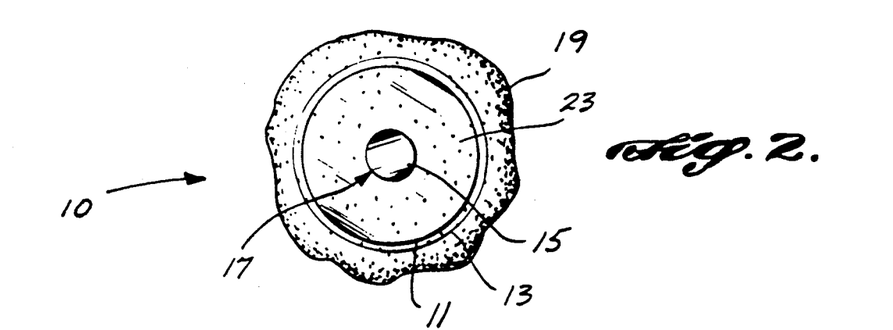
FIG. 2 is a transverse view illustrating the distal end of the sensor of FIG. 1.

A first preferred embodiment of the fiber-optic sensor is shown in FIGS. 1 and 2, generally at reference numeral 10. Sensor 10 includes an optical fiber 11 encased within a polyimide sheath 13, which covers the entire optical fiber 11, except for an exposed portion that extends beyond polyimide sheath 13. In this embodiment, the portion of the optical fiber that extends beyond polyimide sheath 13 is preferably about 600 micrometers in length. The distal end of optical fiber 11 has a generally planar circular surface 23, which is cleaved substantially perpendicular to the longitudinal axis of optical fiber 11. Bonded to circular surface 23 of optical fiber 11 is a cylindrical carbon dioxide ($CO_2$) pellet 17, having a first circular surface 24 disposed directly adjacent to and substantially centered on circular surface 23 of optical fiber 11.

Disposed on a second circular face 25 of the $CO_2$ pellet is a thin film of reflective material 15 (preferably comprising gold foil), which is provided to reflect a light signal propagated through optical fiber 11. Reflective material 15 is substantially concentric with second circular surface 25. It can be appreciated that reflective material 15 and circular surface 25 of optical fiber 11 must be substantially perpendicular to the longitudinal axis of optical fiber 11 to reflect light transmitted through optical fiber 11 and incident on reflective material 15 back into and along the longitudinal axis of the optical fiber. $CO_2$ pellet 17 preferably has a longitudinal thickness on the order of 50 micrometers. $CO_2$ pellet 17 comprises a $CO_2$ analyte indicator molecule codissolved within a polymer matrix, producing a $CO_2$ sensitive material 18 that absorbs light of a predefined wavelength to an extent that depends on the concentration of $CO_2$ around $CO_2$ pellet 17. $CO_2$ pellet 17 is attached to the distal end of optical fiber 11 using one of the methods described below. A light pulse conveyed through optical fiber 11 is absorbed as a function of $CO_2$ concentration around the sensor and is reflected back into the optical fiber by reflective material 15.

A coating 19 of a polymer matrix that incorporates an oxygen quenchable phosphorescent indicator molecule, such as porphyrin, surrounds the entire distal end of optical fiber 11 in the first preferred embodiment of the sensor shown in FIGS. 1 and 2. The relatively high molecular weight porphyrin is insoluble in aqueous solutions and therefore need not be covalently bonded to the polymer matrix. The specific phosphorescent indicator molecule is preferably selected from among platinum or palladium derivatives of tetrafluorophenylporphyrin, octaethylporphyrin, tetraphenylporphyrin, tetraenzporphyrin, tetrafluorobenzporphyrin, and tetrachlorobenzporphyrin. Particularly preferred are photostable, fluorinated derivatives of such metallaporphyrins. In the physiological oxygen pressure range of 0-150 torr, platinum tetraphenylporphyrin provides a lifetime curve that is especially suitable for determining $O_2$ concentration. A preferred method for making coating 19 by mixing the porphyrin into the polymer matrix is described below.

Since $CO_2$ pellet 17 covers a relatively small portion (i.e., less than half) of circular surface 23 at the distal end of optical fiber 11, the remaining surface area of circular surface 23 enables light pulses to readily reach coating 19 and to excite the porphyrin contained therein into phosphorescence. The phosphorescent light emitted by the porphyrin also readily enters the exposed portion of circular surface 23 and is conveyed down the optical fiber for determination of its decay time to measure the $O_2$ level around the sensor.

Figure 3:
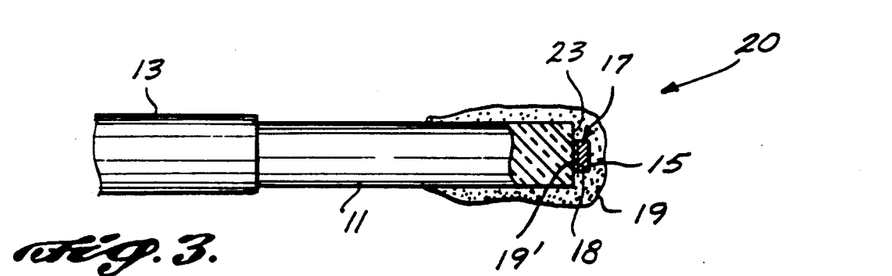
FIG. 3 is a longitudinal view of a second embodiment of the sensor shown in FIGS. 1 and 2.

Alternatively, as shown in FIG. 3, a thin layer 19' of the polymer matrix and porphyrin used in coating 19 can be applied between first circular surface 24 of $CO_2$ pellet 17 and circular surface 23 of the optical fiber to form a sensor 20. $CO_2$ pellet 17, thin layer 19' and the distal end of optical fiber 11 are then covered with coating 19, as in sensor 10. In sensor 20, thin layer 19' and coating 19 are both excited to phosphorescence by light traveling through optical fiber 11 and the duration of the phosphorescence decreases in proportion to the $O_2$ concentration around sensor 20. $CO_2$ pellet 17 responds to the concentration of $CO_2$ just as in sensor 10, i.e., a light pulse propagated down the optical fiber is absorbed by $CO_2$ sensitive material 18 as a function of $CO_2$ concentration around sensor 20, and the intensity of the light pulse reflected by reflective material 15 serves as a measure of that analyte concentration.

Figure 4:
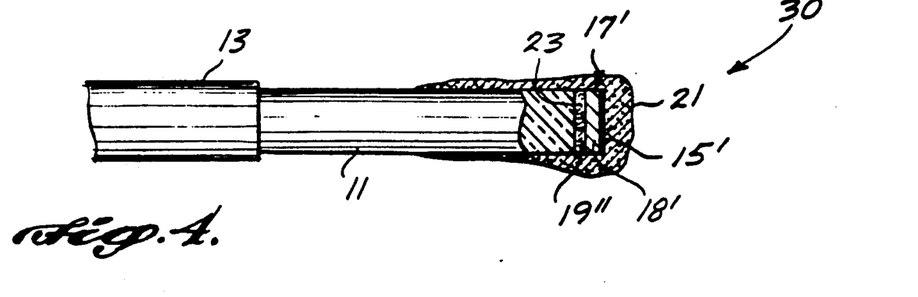
FIG. 4 is a longitudinal view of a third embodiment of the sensor shown in FIGS. 1-3.

With reference to FIG. 4, a third embodiment of the invention is shown, generally represented at reference numeral 30. In this embodiment, sensor 30 includes a relatively thick layer 19" (compared to layer 19' of sensor 20) of polymer matrix in which porphyrin is mixed, that covers substantially the entire surface 23 at the distal end of optical fiber 11. Adherently attached to layer 19" is a $CO_2$ pellet 17', which has a diameter approximately equal that of the optical fiber. Layer 19" and $CO_2$ pellet 17' are about equal in thickness (e.g., on the order of 50 micrometers) as measured along the longitudinal axis of the optical fiber. The entire distal end of optical fiber 11, including $CO_2$ pellet 17' and layer 19", is encased in a hydrophobic coating 21, which is permeable to both $O_2$ and $CO_2$ gases, the two analytes of interest. Coating 21 thus envelopes the distal end of sensor 30 and provides improved structural stability. Preferably, SC-35 silicone (source—Huls America) is used for coating 21.

Figure 5:
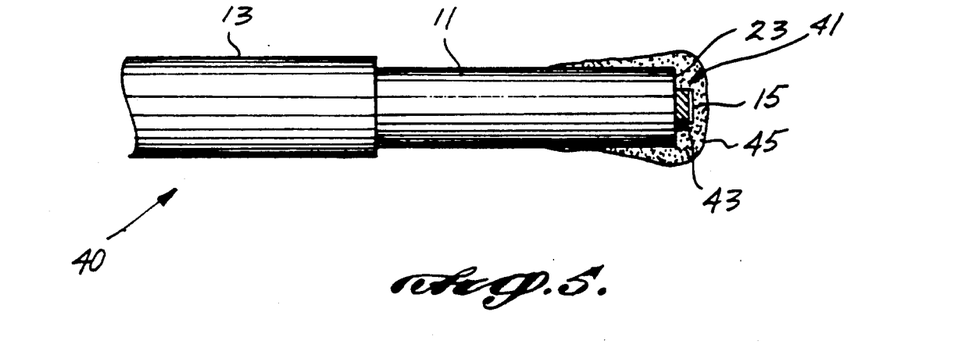
FIG. 5 is a longitudinal view of a fourth embodiment of the sensor used to measure pH and oxygen concentration.

A sensor 40 is shown in FIG. 5 for use in sensing pH and $O_2$ concentration. Sensor 40 appears similar to sensor 10, but differs in two significant ways. Specifically, a pH pellet 41 replaces $CO_2$ pellet 17 and a hydrophilic coating 45 containing porphyrin (or another $O_2$ sensitive indicator) encloses pH pellet 41 and the distal end of optical fiber 11, instead of coating 19. Coating 45, which is hydrophilic, must be used instead of the hydrophobic polymer matrix comprising coating 19 to enable water-carrying hydrogen ions to reach pH pellet 41, so that it can measure the pH of fluid surrounding sensor 40. Preferably, coating 41 comprises cellulose acetate with porphyrin dissolved in it. Although not shown, sensor 40 may be modified to include a thin layer of the polymer coating with porphyrin, which is used to attach pH pellet 41 to the configuration of circular surface 23 of the optical fiber (in a manner analogous to the configuration of sensor 20 in FIG. 3).

Light passing through optical fiber 11 in sensor 40 passes through the portion of circular surface 23 that is not covered by the pH pellet and excites the porphyrin in coating 45 to phosphorescence. The phosphorescent emissions decay over a time interval that decreases as a function of the $O_2$ concentration, so that the phosphorescent light traveling back through the optical fiber can be used to determine $O_2$ concentration, just like in sensor 10.

The pH of fluid surrounding sensor 40 causes a change in the absorption of light of a specified wavelength that is conveyed through optical fiber 11 by a pH sensitive indicator material 43 within pH pellet 41. The light is reflected by reflective material 15 back through pH sensitive indicator material 43 and into the optical fiber. Details concerning the method of making pH pellet 41 and its composition are described below.

Figure 6:
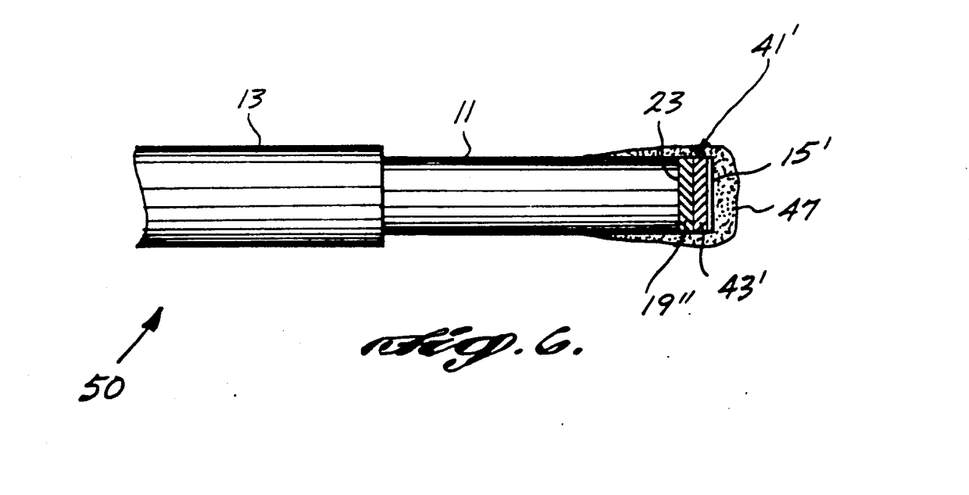
FIG. 6 is a longitudinal view of a fifth embodiment of the sensor, also for use in measuring pH and oxygen concentration.

In FIG. 6, another embodiment of the present invention is shown for monitoring pH and $O_2$ concentration. A sensor 50 is illustrated therein that appears similar to sensor 30 in FIG. 4. However, generally the same differences exist as noted above in comparing sensor 40 to sensor 10. In sensor 50, a pH pellet 41' is attached to layer 19" of the polymer matrix containing porphyrin at the distal end of optical fiber 11. Layer 19" is about the same thickness as pH pellet 41', and both are approximately the same diameter as optical fiber 11. A hydrophilic coating 47 encloses the pH pellet, layer 19" and the distal end of the optical fiber. Coating 47 is hydrophilic, freely permitting the two analytes of interest, i.e., hydrogen ions in water (determinative of pH) and $O_2$, to pass from an external fluid into sensor 50. In the preferred embodiment of sensor 50, coating 50 comprises methacrylamidopropyltrimethylammonium chloride (MAPTAC).

Chemical Composition and Fabrication of Indicator Matrixes $CO_2$ pellets 17 and 17' and pH pellets 41 and 41' generally comprise an analyte indicator molecule codissolved within a polymer matrix that is applied to the light reflective material. Specifically, $CO_2$ pellets 17 and 17' comprise sodium bicarbonate, a $CO_2$ analyte indicator molecule such as phenol red, and the polymer matrix, all coupled with the thin film of reflective material 15 or 15'. Similarly, pH pellets 41 and 41' comprise the pH analyte indicator molecule, also phenol red, and the polymer matrix, all coupled with a thin film of reflective material.

The base polymer matrix is identical for the pH and $CO_2$ pellets and the choice of materials for the polymer matrix is influenced by the need to simultaneously satisfy many requirements. For pH pellets 41 and 41', the polymer matrix must immobilize the indicator molecule in the light path defined by the axial core of the optical fibers. Otherwise, signal drift will result due to leakage of indicator molecules from the polymer matrix, especially leakage of water soluble molecules such as phenol red. The water soluble indicator molecules must therefore be covalently bonded to a component of the polymer matrix. However, $CO_2$ pellets 17 and 17' need not be covalently bonded since the porphyrin and polymer matrix (more fully described below) comprising coating 19, which encapsulates $CO_2$ pellets 17 and 17', are comprised in part of a hydrophobic silicone material. Thus, $CO_2$ pellets 17 and 17' will not be exposed to aqueous liquids and, therefore, the phenol red will not leak from the polymer matrix.

Further, the polymer matrix must also permit free bidirectional movement of the subject analyte, i.e., the polymer matrix must be permeable to the $CO_2$ and pH analytes. For physiological applications in which the analyte is dissolved or dispersed in aqueous solutions, for example, as ionic hydrogen, the polymer matrix must be hydrophilic as well as porous to the analyte substance. However, the hydrophilicity of the polymer matrix must be regulated to prevent undue swelling, with attendant risk of dissociation from the fiber end, when the optical fiber is immersed in aqueous solutions such as blood, lymph fluid, extracellular fluid, and/or serum. Furthermore, swelling in an aqueous solution should not cause differential movement of the polymer matrix, vis-a-vis the light transmitting fiber core, particularly during use of the sensor.

The polymer matrix should have a refractive index that is sufficiently matched to that of the optical core to minimize light scattering effects, such as Fresnel losses, and must be capable of sustaining its attachment onto the end of optical fiber 11. In addition, the polymer matrix should not shrink or crack upon drying. The polymer matrix should also retain its rigidity and strength during use, e.g., by having sufficient wet mechanical strength to maintain its integrity while being manipulated through blood vessels.

A material that satisfies the foregoing requirements for the polymer matrix is made by copolymerizing a mixture of about 94 mole percent (mole %) methyl methacrylate (MMA) and about 6 mole % methacrylamidopropyltrimethylammonium chloride (MAPTAC) as disclosed in U.S. Pat. No. 4,434,249. Polymethyl methacrylate-based material is an especially appropriate matrix component, because it provides a good refractive index match when used with plastic optical fibers having methacrylate cores. This copolymer is highly permeable to water and small ions, especially anions, while meeting all the other requirements mentioned above. Methylmethacrylate can alternatively be copolymerized or alloyed with other ionogenous or neutral monomers, such as hydroxymethyl methacrylate, N-vinylpyrrolidone, or acrylic acid, to confer analyte permeability to the resulting polymer matrix. N-vinylpyrrolidone/p-aminostypene copolymer 60:40 to 80:20 wt./wt. is another suitable resin material. Suitable solvents for these resins are known to include alcohols, N,N-dimethylacetamide (DMAC), N,N-dimethylformamide, methyl ethyl ketone, tetrahydrofuran, esters, and aromatic and chlorinated hydrocarbons.

The indicator molecule is selected to respond optically to the presence of the targeted analyte (e.g., $CO_2$ or pH) when immobilized in the polymer matrix. For continuous monitoring of analyte concentration, the reaction or response between the indicator molecule and the analyte should be reversible as well as sensitive and specific. Suitable analyte-sensitive indicator molecules for other analytes besides $CO_2$ and pH are well known in the art.

As noted earlier, in pH pellets 41 and 41', covalent bonding functions to immobilize water-soluble indicator molecules within the polymer matrix but otherwise must not significantly adversely impact upon the sensitivity, specificity, and reversibility of its optical response to the targeted analyte. Thus, analyte sensitive sites on the indicator molecule must not be eliminated or sterically hindered upon covalent binding to the resin. The indicator molecule should therefore be uniformly bound to the resin in a site-specific manner that preserves the optical responsiveness of the indicator to the analyte, using a reaction protocol that prevents or substantially eliminates heterogenous reaction products.

For this purpose, aminoarylalkylamines are preferably employed to covalently link the indicator molecule to a polymer, which is thereafter admixed in solvent with other matrix components to form an emulsion or solution. Suitable aminoarylalkylamines have the formula:

wherein Ar is nonsubstituted or preferably substituted phenyl and n is an integer. Preferably, n equals 2 or 3 in order to avoil hydrocarbon characteristics associated with longer alkyl chains. The aminoarylalkylamine is preferably para-substituted. Exemplary aminoarylalkylamines for practicing the invention are 4-(aminophenyl)-ethylamine and 4-(aminophenyl)-(propellamine).

Heterogeneous reaction products are prevented by specifically attaching the alkylamino moiety to the polymer before reacting the arylamino moiety with the indicator molecule. The aminoarylaklylamine is first attached to a polymeric resin component, such as MMA/MAPTAC, by reaction in ethanol at 70° C. with triethylamine as a catalyst. The free arylamino group is then reacted with the indicator molecule of choice, for example, by using a diazotization for coupling with indicator molecules such as phenol red that have strong electron releasing groups, or by formation of an amidyl linkage with carboxylic acid bearing indicator molecules. The available diazonium binding sites should be saturated with an excess of indicator molecules during this second reaction step, in order to provide a polymeric resin component containing a concentrated amount of indicator molecule.

The $CO_2$ indicator molecules need not be covalently bonded to the polymer matrix. In the exemplary formation of the $CO_2$ pellets 17 and 17' without covalent bonding, the following protocol may be followed: One gram of solid PEG 600 k is dissolved in 19 grams of 2-methoxyethanol (5% wt./wt.) and stirred or sonicated until homogeneous. The solution of MMA/MAPTAC (94:6) is prepared by dissolving one gram of solid MMA/MAPTAC in 6.7 grams of 2-methoxyethanol (13% wt./wt.) and stirring until homogeneous. Next, 3.07 grams of the 13% MMA/MAPTAC solution is mixed with 2 grams of the 5% PEG 600 k solution. The ratio of the solid MMA/MAPTAC to solid PEG 600 k is 80% to 20%. The admixed solution may be sonicated for up to five minutes to insure a homogeneous solution. To this mixed solution, 0.005 grams of phenol red is added and stirred until homogeneous. Finally, 200 microliters of 0.875 Molar bicarbonate solution is added to the phenol red and the MMA/MAPTAC solution to form the $CO_2$ polymer matrix solution used to make a $CO_2$ analyte sensitive material 22. In an alternative approach, the $CO_2$ analyte indicator molecule may be covalently bonded with the MMA/MAPTAC polymer using the aminoarylalkylamines noted earlier to form the $CO_2$ polymer matrix solution.

Regardless of the particular polymer matrix solution used, chemically bonded or admixed, the next step in the manufacture of the $CO_2$ pellets 17 and 17' consists of applying the $CO_2$ polymer matrix solution to a reflective material such as gold foil. Suitable gold foil is available in 1-inch by 12-inch strips that are shipped on a plastic roll. The gold foil is prepared by placing the foil between two clean glass slides and cutting away a 1-centimeter by 2½-centimeter strip. The strip is cut in half once again, such that there are two 1-centimeter by 1.25-centimeter pieces. The thickness of each foil piece is measured using, e.g., a Mitutoyo Digital Micrometer, and the foil pieces are checked for uniformity before being placed in a scintillation vial to which 1 ml of concentrated HCl is added. The foil is allowed to soak in the concentrated HCl for at least two hours, but preferably for 8-12 hours to remove any residues on the gold foil surface. The gold foil is removed from the vial of concentrated HCl, and rinsed with copious amounts of distilled water, at least three times on each side. After being rinsed, the gold foil is placed on a glass slide, and any moisture is removed from the gold surface with blotting paper. Finally, the gold foil is examined for shininess or impurities. (If spots/impurities do appear on the gold foil, it is replaced in the concentrated HCl and the cleaning process repeated.)

Using adhesive tape, the gold foil is attached to a glass slide. Preferably, the gold foil is taped down such that the surface of the foil is flat (by stretching the gold foil after it is taped down), and a 1-centimeter by 1-centimeter area of the gold foil is exposed. The tape is next masked to prevent the dye solvents from dissolving the tape mount and, hence, destroying the film prep. A bead of UV-curable adhesive (e.g., NOA-81 supplied by Norland Products, Inc., New Brunswick, NJ) is placed along the tape on both sides of the gold foil. Using a No. 2 paint brush, the adhesive is brought over the tape and up to, but not onto the surface of the gold foil. Should the NOA-81 adhesive leach onto the gold foil surface, the adhesive is cured under a 365 nm UV lamp, peeled away, and the NOA-81 again applied. Once the NOA-81 has been brought to the edge of the gold foil on both sides, such that it completely covers the tape, but does not extend the gold foil surface, the adhesive is cured by placing it under a 365 nm UV lamp for about five minutes.

A leveling plate is placed on top of a Corning hot plate/stirrer, which is set to provide a temperature of about 45°-55° C. A two-way level is used to adjust the height of the screws on the leveling plate until the plate is level. The glass slide containing the gold foil mount is placed onto the leveling plate and allowed to achieve temperature equilibrium. The solution of the polymer matrix and the $CO_2$ indicator molecule as produced by the process described earlier are placed into an oven and allowed to reach 45° C. A 50-microliter aliquot of the polymer matrix (10% wt./wt.) solution is placed onto the surface of the gold foil with a micropipette. The micropipette tip can be used to brush the dye over the entire surface of the gold. However, care should be taken such that the dye is not applied beyond the foil edge. Should this happen, the sample is removed and the application repeated with a new foil mount. Any bubbles in the film surface should be removed by blowing air through the micropipette tip.

The measured amounts of dye given for the film preps here are based on an exposed gold area of one square centimeter. For mounted foils having exposed surface areas other than one square centimeter, the exposed area is multiplied by the amount of dye given for one square centimeter, and that amount of dye is applied to the foil surface.

Next, a 7-centimeter drying tube is placed over the sample. The leveling plate and the gold foil are left undisturbed, allowing approximately two hours for the film to dry. After the drying process is complete, the gold foil must be cut from the glass slide and measured for thickness to assure uniformity. Using adhesive tape, all four sides of the gold film should next be attached to the counter, allowing the tape to cover about 1 millimeter of the film on each side. Using the end of a bull-nosed tweezers, the adhesive tape is secured to the film by compressing the tape down onto the film surface, being careful not to scrape the film surface. Any excess tape is trimmed so that the film mount is square. The film mount is removed from the counter and inverted onto a glass slide. Thin strips of adhesive tape are placed around the underside of the film such that the tape extends over the gold surface, but not beyond the tape on the film side of the sample. Again, the end of the bull-nosed tweezers is used to compress the tape securely against the foil. The film mount is centered onto the micro punch XY plate, dye side up, and taped to the XY plate such that the film lies flat and there are no folds in the adhesive tape. The underside of the sample is checked to be sure that the gold foil is clean prior to securing the XY plate to a micro punch (e.g., Model #001, Abbott Research, Inc., Bothell, Wash.). $CO_2$ pellets 17 and 17' that are punched from the coated gold foil are then used in the construction of the sensor by attaching the $CO_2$ pellet to the distal end of the optical fiber.

In a similar manner, pH pellets 41 and 41' are constructed. A pH indicator molecule, such as phenol red, is codissolved with the same polymer matrix that was used in making the $CO_2$ pellets. Because phenol red is water soluble and pH pellets 41 and 41' are exposed to aqueous fluids during use, it must be covalently bonded to the polymer matrix. Thus, as stated earlier, an aminoarylalkylamine is used to effectuate the covalent bonding. In one embodiment, 4-(amino phenol)-ethylamine (APE) is attached to the MMA/MAPTAC polymer. Initially, the APE is purified as the dihydrolchloride by taking 4 grams of APE (Aldrich Chemical Company, Inc., Milwaukee, Wis.) in 8 milliliters of concentrated hydrochloric acid at 0° C. and recrystallizing the dihydrolchloride from water ethanol (100 milliliters of 95:5 water-ethanol). Next, 2 millilieters of 10% MMA/MAPTAC solution is azeotroped with anhydrous ethanol (using three 50-milliliter aliquots) and redissolved in 25 milliliters anhydrous ethanol. 0.38 grams of the APE-dihydrolchloride and 1 milliliter of freshly distilled triethylamine as a catalyst are then added, and the solution is stirred in an oven at 55° C. for 48 hours. The solvent and excess triethylamine are removed in a rotary evaporator.

The MMA/MAPTAC polymer with the APE attached is used as the medium for carrying the phenol red indicator molecule. The coupling of the phenol red to the APE/MMA/MAPTAC is accomplished as follows. The APE/MMA/MAPTAC reaction product is dissolved in 20 milliliters of denatured ethanol at 0° C., and to that solution is added 3 milliliters of concentrated HCl and 3 milliliters of water. Next, a solution of 0.3 grams of $NaNO_2$ in 2 milliliters of water is added and the resulting solution stirred at 0° C. for three hours. This entire solution is then added to 2.4 grams of phenol red and 2.5 grams of $KHCO_3$ in 30 milliliters of water and 30 milliliters of denatured ethyl alcohol, while stirring at 0° C. It is important when coupling the diazotized APE polymer to phenol red, to maintain a pH of the solution at about 8.5 using $KHCO_3$, and to use excess phenol red to saturate all diazotized sites and prevent diazonium hydroxide/phenol formation. The resulting solution is stirred overnight at 0° C.

The solution produced by the preceding coupling reaction is brought to a pH of 1.0 with concentrated HCl at 0° C., and 500 milliliters of ice cold water is added. The product is filtered and the residue from the filtration is washed with water (three aliquots of 100 ml). The washed residue is mixed with 2.5 grams of $KHCO_3$ and 250 milliliters water and a stirred cell separation is conducted using a F-type membrane (Spectrum Ultra-por, Type F MWCO:50,000, Spectra Medical Industries, Los Angeles, CA) under nitrogen gas. The ultrafiltration is continued until the filtrate is colorless, as indicated by nonabsorption of light having a wavelength of 570 nanometers. The reddish-brown pure filtered residue product is dried in a dessicator and is referred to as PR/APE/MMA/MAPTAC (PAMM).

Next, sufficient PAMM is added to a 10% solution of MMA/MAPTAC solvent (acid form) in N,-dimethylacetamide (DMAC) to produce a solution with 15% PAMM by weight. (This solution may be used to overcoat pH pellet 41' to produce coating 47 and is referred to as "DEF-1.") A 5% solution of polyethylene oxide (PEO) in DMAC is added to part of this solution in sufficient quantity to produce a solution that is from 1-3% PEO solids by weight, producing a solution (referred to as "DEF-1 with PEO") used to form pH sensitive indicator material 43.

The preparation of the gold foil for producing pH pellets 41 and 41' is identical to that described above in respect to $CO_2$ pellets 17 and 17'. The gold foil is placed on a clean glass slide and adhesive tape is used to anchor two opposite sides of the gold foil to the glass slide. The gold foil is secured such that the surface of the foil is flat and the distance between the two pieces of tape is 1 square centimeter. Excess adhesive tape is removed with a razor blade by cutting along the edges of the foil, which are not taped. Next, adhesive tape is placed over the other two sides of the foil such that the total exposed area of the gold foil is 1 square centimeter; the final two pieces of tape extend over the first two pieces of tape (which are trimmed off right at the foil edge). Bull-nosed tweezers are used to compress the edges of adhesive tape down on the gold foil. Any air pockets between the pieces of adhesive tape and the glass slide and foil are removed.

To form the borders around the foil-backed area that will receive the dye, a bead of NOA-81 adhesive is placed along the tape on two sides of the gold foil. By using a No. 2 paint brush, the adhesive is brought over the tape and right up to the surface of the foil. The adhesive is allowed to cure for about 5 minutes. It can be appreciated that after the application of the adhesive onto the taped surfaces on all four sides of the gold foil, a recess is formed on top of the gold foil such that when the polymer matrix with analyte indicator is applied to the gold foil, the polymer matrix will tend to stay within the borders of the gold foil.

Next, 135 microliters of the DEF-1 with 1-3% PEO in solution is applied over the gold surface with a digital micropipette. The coated gold foil mount is placed on a hot plate set to a temperature of from 45°-55° C. and dried for about two hours. The resulting coated gold foil is cut from the glass slide, mounted for punching, and punched immediately. The mounting and punching protocol is identical to that of the $CO_2$ pellet discussed above. After the pH pellets are thus manufactured, they may be used in the production of the sensor of the present invention.

An $O_2$ indicator solution, such as used for coating 19 and for layers 19' and 19", is prepared for sensing the oxygen analyte. However, the $O_2$ carrier polymer matrix is unlike the polymer matrix used for the $CO_2$ and pH pellets. A hydrophobic silicone material, such as SC-35 (Huls America), is used for the $O_2$ polymer matrix in sensors 10, 20, 30, and 50. A suitable oxygen analyte indicator molecule is porphyrin. Due to its relatively high molecular weight, porphyrin is insoluble in aqueous solutions and so need not be covalently bonded to the polymer matrix with which it is applied.

A typical protocol for the mixture of the porphyrin indicator molecules into the $O_2$ carrier polymer matrix is as follows. First, 0.25 grams of SC-35 silicone and 0.012 grams PtTFPP (Porphyrin Products, Logan, Utah) are weighed and mixed together. Next, 2.36 grams of tetrahydrofuran is added to the above constituents. This process results in a 10 percent solution of an oxygen indicator PT55, which when solidified, is hydrophobic, but gas permeable, and is used to form coating 19 and layers 19' and 19".

A typical protocol for the mixture of the porphyrin indicator molecule into the polymer matrix is described as follows. First, 0.25 grams of SC-35 silicone (Huls America) and 0.012 grams PtTFPP (Porphyrin Products, Logan, Utah) are weighed and mixed together. Next, 2.36 grams of tetrahydrofuran are added to the above constituents. This process results in a 10% solution of an oxygen indicator, referred to as "PT55," which, when solidified, comprises the $O_2$ sensitive indicator used in coating 19 and in layers 19' and 19".

To encase the entire distal end of optical fiber 11 in coating 19 as required to form sensors 10 and 20, optical fiber 11 with $CO_2$ pellet 17 already adherently attached (using a suitable transparent adhesive in the case of sensor 10 and with layer 19' in sensor 20) is hand-dipped into the PT55 solution until a built-up thickness of about 120 micrometers is achieved. Construction of sensor 10 is completed by drying the PT55 solution overcoat on the distal end of optical fiber 11, forming coating 19.

To form sensor 30, layer 19' is applied to the distal end of optical fiber 11 and $CO_2$ pellet 17' is adherently attached to layer 19' before it dries. The entire distal end of the optical fiber is then dipped into and coated with SC-35 silicone, built up to a thickness of about 120 micrometers.

Sensor 40 is constructed by adherently attaching pH pellet 41 so that it is concentrically centered in circular surface 23 at the distal end of optical fiber 11. The pH pellet and distal end of the optical fiber are then dipped into the cellulose acetate solution containing porphyrin to form coating 45. Porphyrin is mixed with the hydrophilic polymer to form this solution following an analogous technique to that described above for mixing it with SC-35 silicon; however, cellulose acetate is substituted for the silicon.

The same steps are generally followed to form sensor 50 as employed in making sensor 30, except that pH pellet 41' is adhered to layer 19" and the distal end of the optical fiber is coated with MAPTAC solution to form coating 47 when dried. Alternatively, coating 47 may comprise DEF-1.

Figure 7:
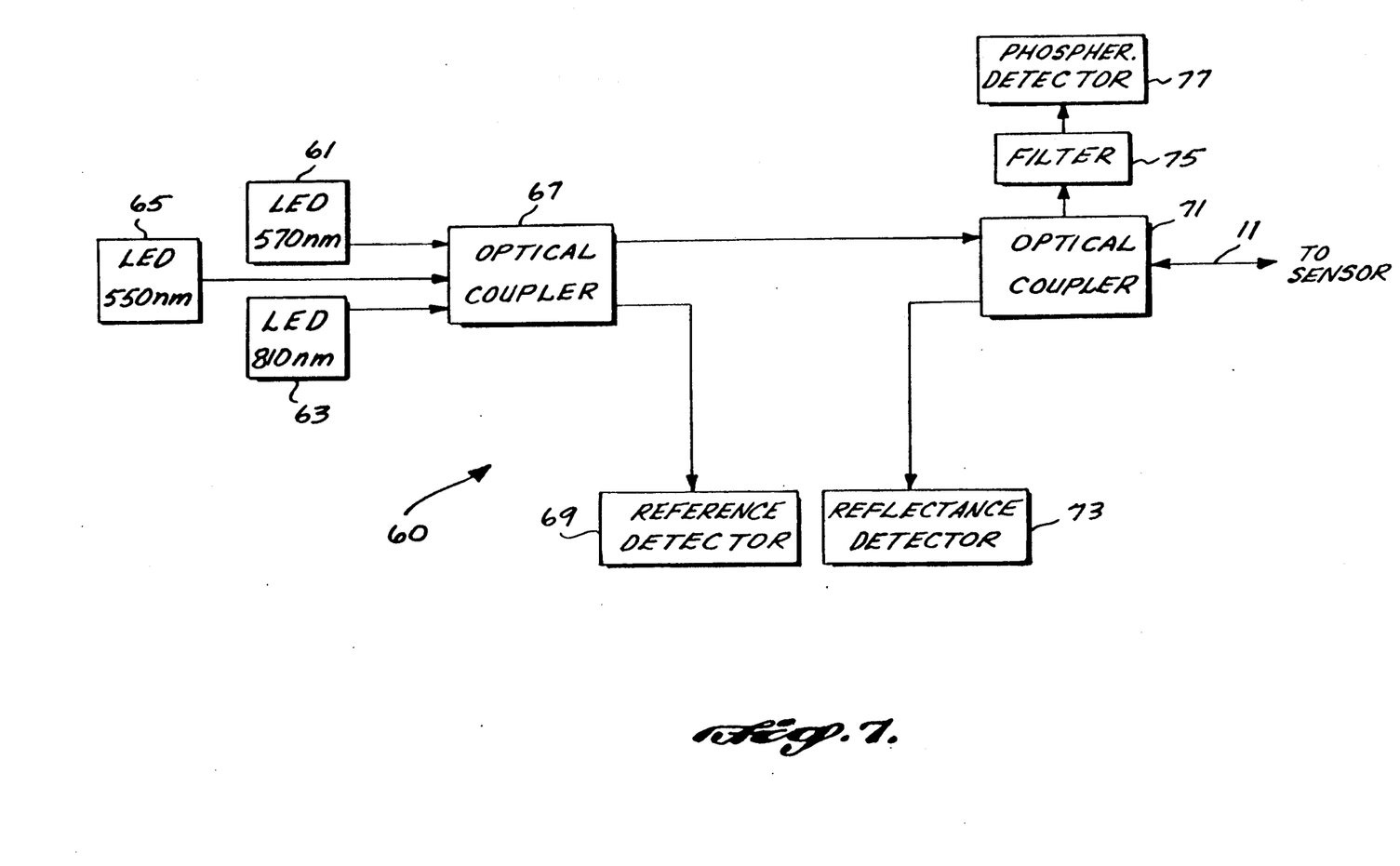
FIG. 7 is a block diagram of a system for use with any of the embodiments of the sensor to measure oxygen and either carbon dioxide concentration or pH.

With reference to FIG. 7, an optical fiber physiological blood gas concentration sensing system 60 is shown that is usable with all of the embodiments of the sensor disclosed above. The illustrated system comprises a light emitting diode (LED) 61 that produces light having a wavelength of about 570 nm and an LED 63, producing light having a wavelength of about 810 nm, which together are used by system 60 in determining either pH or $CO_2$ concentration, depending on which sensor is employed. An LED 65 produces light having a wavelength of about 550 nm for use in the sensor in determining $O_2$ concentration. LED 61 generates a short pulse of light, which propagates into an optical coupler 67, where the light signal is split into two branches, one branch passing the light pulse into a reference detector 69 and the other branch conveying the light pulse towards an optical coupler 71.

The reference detector monitors the amplitude of the light pulse produced by LED 61 and produces a signal that is used for compensating variations in the output LED 61. The light pulse from LED 61 that is conveyed to the sensor passes bidirectionally through the $CO_2$ pellet in the case of sensors 10, 20, or 30, or through the pH pellet in the case of sensors 40 or 50, and is reflected by reflective material 15 or 15'. Depending upon the extent to which the light is attenuated as a function of the pH or $CO_2$ concentration in the surrounding fluid, light at the 570 nm wavelength is attenuated and reflected back into optical fiber 11. The reflected light pulse is directed by optical coupler 71 to a reflectance detector 73, which monitors the amplitude of the reflected light pulse at the 570 nm wavelength. A second light pulse is emitted from LED 63 follows the same dual paths from optical coupler 67 to reference detector 69, and to optical coupler 71. Optical fiber 11 conveys this light pulse to the sensor. As light at the 810 nm wavelength passes through either the $CO_2$ or pH pellet (depending on the sensor in use), it is NOT attenuated as a function of the concentration of the applicable analyte. The light pulse at the 810 nm wavelength thus serves as a reference signal that is reflected back to optical coupler 71 through optical fiber 11. Optical coupler 71 directs this reflected light pulse into reflectance detector 73, which measures its amplitude. By comparing the amplitude signal produced by reflectance detector 73 in response to light at the 570 nm wavelength against the reference signal produced by the reflectance detector in response to the reflected light pulse at the 810 nm wavelength, a measure of the absorption by the analyte of interest may be determined. The signals from reference detector 69 are used to compensate for losses in system 60. Consequently a $CO_2$ concentration pH level may be calculated, depending on which sensor is employed.

The operation of the $O_2$ sensing portion of the system is slightly different. Following the light pulses from LEDs 61 and 63, LED 65 produces a light pulse of a wavelength chosen to excite phosphorescence in the $O_2$ analyte indicator material in coatings 19 or 45, or layers 19' or 19''. Once again, the transmitted light signal travels through optical coupler 67 to optical coupler 71 and on to the sensor. At the distal end of optical fiber 11, the phosphorescence of the oxygen analyte indicator matrix, i.e., porphyrin, decays at a rate dependent upon the concentration of $O_2$ present. This phosphorescent light signal is conveyed by optical fiber 11 into optical coupler 71, whereby the signal is directed to a passband filter 75 having a center frequency of about 650 nm, wavelength of the phosphorescent light. The blocks light of other wavelengths, but passes the phosphorescent light to a phosphorescent detector 77. By measuring the phosphorescence decay time, the oxygen gas concentration is determined. The higher the concentration of $O_2$ to which the sensor is exposed, the faster the phosphorescence is quenched.

While certain preferred embodiments of the invention have hereinbefore been described, it will be appreciated that other variations to the invention will be perceived by those skilled in the art, which variations are nevertheless within the scope of the claims appended hereto.

The embodiments of the invention in which an exclusive property or privilege is claimed are defined as follows:

1. A probe for monitoring a plurality of chemical parameters comprising:
   (a) an optical fiber having a longitudinal axis along which light signals at a plurality of wavelengths are propagated bidirectionally;
   (b) an optical sensor attached adjacent to a distal end of the optical fiber, said sensor comprising a first analyte indicator, light signals of a first wavelength being absorbed by the first analyte indicator to an extent dependent upon the amount of a first analyte present; and
   (c) a polymer matrix material in which a second analyte indicator is provided, said polymer matrix material being disposed adjacent to the distal end of the optical fiber and adjacent the optical sensor, light signals of a second wavelength transmitted to the distal end of the optical fiber exciting the second analyte indicator to emit light, a decay time of the light emission varying in response to a concentration of the second analyte.

2. The probe of claim 1, wherein the first analyte indicator is sensitive to a carbon dioxide concentration.

3. The probe of claim 1, wherein the first analyte indicator is sensitive to a pH level.

4. The probe of claim 1, wherein the optical sensor is attached to the distal end of the optical fiber with a thin coat of said polymer matrix material and second analyte indicator.

5. The probe of claim 4, wherein the optical sensor and the distal end of the optical fiber are covered with a coating comprising said polymer matrix material and said second analyte indicator.

6. The probe of claim 1, wherein the optical sensor comprises a pellet attached to a transverse surface of the optical fiber at its distal end, said pellet covering only a portion of the transverse surface, a coating comprising said polymer matrix material and said second analyte indicator enclosing said pellet, said transverse surface, and said distal end of the optical fiber.

7. The probe of claim 1, wherein said polymer matrix material and said second analyte indicator comprises a layer interposed between the optical sensor and the distal end of the optical fiber.

8. The probe of claim 1, wherein the first analyte is carbon dioxide and said first analyte indicator is sensitive to a carbon dioxide concentration.

9. The probe of claim 1, wherein the first analyte comprises hydrogen ions, and said first analyte indicator is sensitive to a pH level.

10. The probe of claim 7, wherein the first analyte is ionized in water, further comprising a hydrophilic coating applied over the layer of said polymer matrix material and second analyte indicator, and over the optical sensor.

11. The probe of claim 7, wherein the first analyte is a gaseous substance, further comprising a hydrophobic coating applied over the layer of said polymer matrix material and second analyte indicator and over the optical sensor.

12. The probe of claim 6, wherein said first analyte is ionized in water, said polymer matrix being hydrophilic and thus permeable to water.

13. The probe of claim 6, wherein said first analyte is a gaseous substance, said polymer matrix being hydrophobic and thus permeable to the gaseous substance.

14. The probe of claim 1, wherein said second analyte is oxygen and said second analyte indicator comprises a porphyrin compound.

15. The probe of claim 1, wherein the second analyte indicator is substantially unaffected by light signals at the first wavelength.

16. A blood gas sensor comprising:
   (a) an optical fiber having a longitudinal axis along which light signals are propagated bidirectionally at a plurality of wavelengths;
   (b) a first polymer matrix material containing a first indicator molecule, said first indicator molecule exhibiting phosphorescence when excited by light of a first wavelength, the duration of phosphorescence depending upon an oxygen gas concentration around the sensor;
   (c) a second polymer matrix material containing a second indicator molecule, said second indicator molecule absorbing light at a second wavelength as a function of a selected chemical parameter; and (d) a light reflectance material disposed adjacent said second polymer matrix material such that light transmitted by said optical fiber is substantially reflected back into said optical fiber, wherein said first polymer matrix material is disposed adjacent to said second polymer matrix material and adjacent the distal end of said optical fiber.

17. The blood gas sensor of claim 16, wherein said second polymer matrix material comprises a pellet that is attached to the distal end of said optical fiber.

18. The blood gas sensor of claim 17, wherein said light reflective material is disposed on a surface of said pellet transverse to the longitudinal axis of the optical fiber such that light is substantially reflected back into the optical fiber by the light reflectance material.

19. The blood gas sensor of claim 18, wherein said pellet is attached to the distal end of said optical fiber by said polymer matrix material.

20. The blood gas sensor of claim 17, wherein said distal end of said optical fiber and said pellet are overcoated with said first polymer matrix material.

21. The blood gas sensor of claim 17, wherein said pellet is smaller in diameter than a transverse area of said distal end of said optical fiber and covers only a portion of said transverse area, said first polymer matrix material completely covering the pellet and a remaining portion of the distal end of said optical fiber that is not covered by the pellet.

22. The blood gas sensor of claim 16, wherein a hydrophobic coating is applied over said distal end of said optical fiber, said first polymer matrix material, said second polymer matrix material, and said light reflective material.

23. The blood gas sensor as claimed in claim 16, wherein a hydrophilic coating is applied over said distal end of said fiber-optic light transmission means, covering said first polymer matrix material, said second polymer matrix material, and said light reflective material.

24. The blood gas sensor as claimed in claim 16, wherein said first indicator molecule is substantially unaffected by light of said second wavelength.

25. The blood gas sensor of claim 16, wherein said first indicator molecule comprises a porphyrin compound.

26. The blood gas sensor of claim 16, wherein the second indicator molecule comprises phenol red.

27. The blood gas sensor of claim 22, wherein the selected chemical parameter is carbon dioxide concentration.

28. The blood gas sensor of claim 23, wherein the selected chemical parameter is a hydrogen ion concentration, expressed in terms of a pH level.

29. An optrode for monitoring blood gases comprising:

(a) an optical fiber for propagating light bidirectionally along a longitudinal axis at a plurality of wavelengths;

(b) a first polymer matrix having a first analyte indicator molecule codissolved within said first polymer matrix, said first polymer matrix being disposed at the distal end of said optical fiber such that said propagated light is incident upon said first polymer matrix;

(c) a second polymer matrix having an $O_2$ analyte indicator molecule codissolved within said second polymer matrix, said second polymer matrix being disposed at the distal end of said optical fiber and separate from the first polymer matrix such that said propagated light is incident upon said second polymer matrix; and (d) a light reflective material disposed at the distal end of said optical fiber such that said propagated light that is incident upon said first polymer matrix is reflected by said light reflective material back into said optical fiber.

30. The optrode of claim 29, wherein the first analyte indicator molecule is sensitive to a carbon dioxide concentration.

31. The optrode of claim 29, wherein the first analyte indicator molecule is sensitive to a hydrogen ion concentration.

32. The optrode of claim 29, wherein said first polymer matrix is formed into a cylindrical pellet and said light reflective material is disposed directly adjacent to a first circular face of said cylindrical pellet, and wherein said cylindrical pellet is attached to a transverse surface of the distal end of said optical fiber at a second circular face of said cylindrical pellet that is opposite the first circular face.

33. The optrode of claim 32, wherein said cylindrical pellet is attached to said distal end of said optical fiber by the application of a thin coat of said second polymer matrix.

34. The optrode of claim 32, wherein said cylindrical pellet and said distal end of said optical fiber are overcoated with said second polymer matrix.

35. The optrode of claim 29, wherein said first analyte indicator molecule comprises phenol red.

36. The optrode as claimed in claim 29, wherein said first analyte indicator molecule comprises a porphyrin compound.

37. A method for making a chemical sensor, comprising the steps of:

(a) mounting a first polymer matrix on at least a portion of a distal end of an optical fiber so that light propagating through the optical fiber passes into the first polymer matrix, said first polymer matrix containing a first indicator molecule, said first indicator molecule absorbing light of a first wavelength in proportion to the concentration of a first analyte;

(b) applying a thin film of light reflective material adjacent to said first polymer matrix such that light of said first wavelength propagated distally along said optical fiber and through said first polymer matrix is reflected by said thin film of light reflective material, said reflected light propagating back towards a proximal end of said optical fiber; and (c) applying to the distal end of said optical fiber a second polymer matrix that is separate from said first polymer matrix, said second polymer matrix containing a second indicator molecule, said second indicator molecule emitting light when excited by light of a second wavelength to an extent that is proportional to the concentration of a second analyte disposed around the sensor.

38. The method of claim 37, wherein said first analyte is carbon dioxide, further comprising the step of coating the first polymer matrix and the distal end of the optical fiber with a hydrophobic material.

39. The method of claim 37, wherein said first analyte to be sensed comprises hydrogen ions, further comprising the step of coating the first polymer matrix and the distal end of the optical fiber with a hydrophilic material.

40. The method of claim 37, wherein the second analyte comprises oxygen, further comprising the step of overcoating the distal end of said optical fiber with a material that is permeable to oxygen gas and to said first analyte, such that said material encompasses said first polymer matrix, said thin film of light reflective material, and said second polymer matrix.

41. The method of claim 37, wherein said first analyte comprises hydrogen ions in water and said second analyte comprises oxygen, further comprising the steps of overcoating the distal end of said optical fiber with a hydrophilic material that is permeable to oxygen gas and water, such that said hydrophilic material encompasses said first polymer matrix, said thin film of light reflective material, and said second polymer matrix.

42. The method of claim 37, wherein said second polymer matrix is applied prior to the step of coating said first polymer matrix such that said second polymer matrix is substantially interposed between the distal end of said optical fiber and said first polymer matrix.

43. The method of claim 37, wherein said first polymer matrix covers only a portion of a transverse area of the distal end of said optical fiber such that light of said second wavelength is incident upon said second polymer matrix through a remainder of the transverse area of said distal end.

44. The method of claim 37, wherein said second polymer matrix is substantially transparent to light signals at said first wavelength and said second analyte indicator is generally unaffected by such light signals.

* * * * *